United States Patent [19]

Freche et al.

[11] Patent Number: 4,970,312

[45] Date of Patent: Nov. 13, 1990

[54] 4,6-DI-2-(5-NITRO-1,2,4-TRIAZOLE)-5-NITROPYRIMIDINE

[75] Inventors: Jean-Paul Freche, Nancy; Francois Laval; Christian Wartenberg, both of Monts, all of France

[73] Assignee: Commissariat A l'Energie Atomique, Paris, France

[21] Appl. No.: 280,598

[22] Filed: Dec. 6, 1988

[30] Foreign Application Priority Data

Dec. 8, 1987 [FR] France .................. 87 17060

[51] Int. Cl.$^5$ .......................................... C07D 413/14
[52] U.S. Cl. ................................. 544/328; 544/245
[58] Field of Search ................... 544/326, 328, 245

[56] References Cited

U.S. PATENT DOCUMENTS 2,987,520 6/1961 Sickman ..................... 260/308
3,483,211 12/1969 Coburn ........................ 260/308
3,923,804 12/1975 Sitzmann et al. ............ 260/251 R

*Primary Examiner*—John M. Ford

*Attorney, Agent, or Firm*—Pearne, Gordon, McCoy & Granger

[57] ABSTRACT

The invention relates to a novel pyrimidine derivative. This derivative is 4,6-di-2-(5-nitro-1,2,4-triazole)-5-nitropyrimidine of formula:

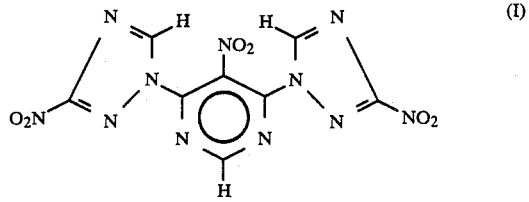

in the form of the pure isomer or mixtures of isomers.

It can be prepared by reacting a dihalogeno nitropyrimidine with 5-nitro-1,2,4-triazole.

It can be used as a secondary explosive.

2 Claims, No Drawings

4,6-DI-2-(5-NITRO-1,2,4-TRIAZOLE)-5-NITROPYRIMIDINE

DESCRIPTION

The present invention relates to a novel pyrimidine derivative, its production process and its use as an explosive.

More specifically, it relates to a novel pyrimidine derivative usable as a secondary explosive for equipping missiles and modern armaments.

For these applications, it is often of interest to use explosives having a minimum shock sensitivity, but a high power, i.e. the capacity to deliver a very high energy. These two properties are difficult to find simultaneously in one and the same explosive. Thus, triaminotrinitrobenzene (TATB) is very insensitive to shocks, but lacks power, whereas cyclotetramethylene tetranitramine (octogen) is very powerful, but is more sensitive to shocks and attacks.

Research has recently been carried out to develop new explosives, whose shock sensitivity is close to that of TATB, whilst they are still able to deliver a higher energy than the latter and which is close to that of octogen.

The present invention relates to a novel pyrimidine derivative having such properties. The novel pyrimidine derivative according to the invention is 4,6-di-2-(5-nitro-1,2,4-triazole)-5-nitropyrimidine in accordance with formula:

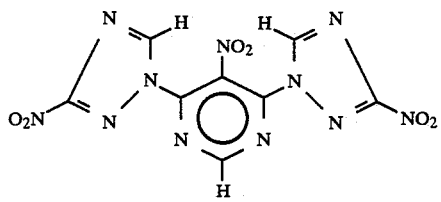

This novel pyrimidine derivative is of considerable interest for use as a secondary explosive, because its explosive or detonating properties are intermediate between those of TATB and those of octogen with regards to the shock sensitivity and the detonation velocity. This novel pyrimidine derivative can be prepared by a process consisting of reacting a 4,6-dihalogeno-5-nitropyrimidine of formula:

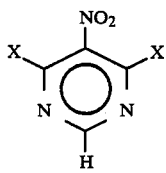

in which X represents fluorine, chlorine or bromine with 5-nitro-1,2,4-triazole of formula:

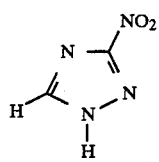

This process is based on a nucleophilic substitution reaction between the 5-nitro-1,2,4-triazole of formula 111 and a 4,6-di halogeno-5-nitropyrimidine of formula 11, which are commercially available starting reagents or reagents which can be easily synthesized. The reaction is simple and fast and corresponds to the following reaction diagram:

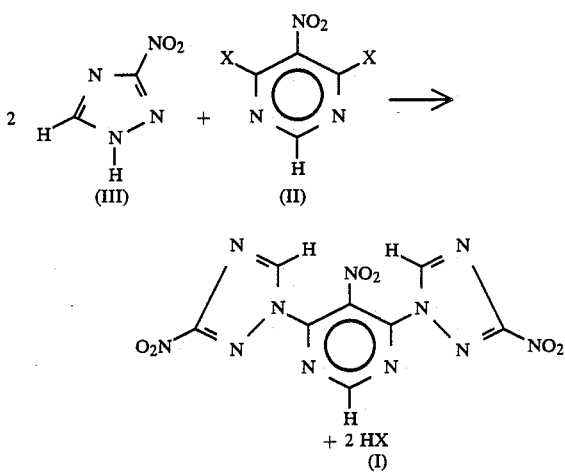

The 5-nitro-1,2,4-triazole of formula III used as the starting product for this reaction is a commercially available product. It can also be easily prepared in the laboratory from 5-amino-1,2,4-triazole, which is a compound produced in large quantities by the phytosanitary and photographic industries. A currently used method consists of carrying out a diazotization by the action of nitrous acid and then a substitution of the diazonium group by the nitrite ion $NO_2^-$. Thus, the aromatic character of the 1,2,4-triazole cycle permits the diazotization by the action of nitrous acid. The substitution of the thus formed diazonium group by the nitrite ion can then take place under the action of an aqueous sodium nitrite solution in accordance with the following reaction diagram:

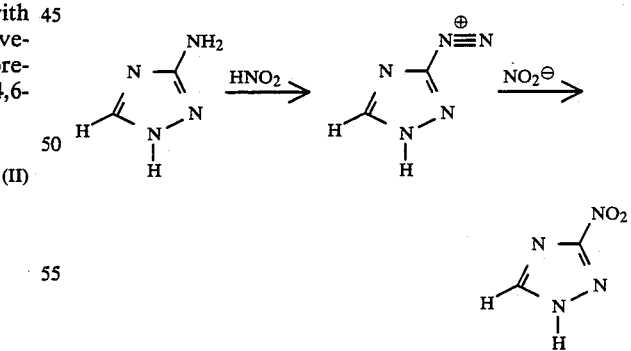

Numerous operating procedures based on these reactions have been described in particular by L. I. Bagal et al in Chemistry of heterocyclic compounds, 6, 265 1970; M. S. Pevzner et al in Khimiya Getero Soedin, 8, 1132, 1979; J. W. Jones et al in J. Al. Chem. Soc. 82, 3773, 1960; E. J. Browne in Aust. J. Chem. 22, 2251, 1969; and J. L. Closset et al in Bull. Soc. Chim. Belg. 84, 1975.

The halogen of the 4,6-dihalogeno-5-nitropyrimidines can be fluorine, chlorine or bromine.

The process according to the invention preferably uses 4,6-dichloro-5-nitropyrimidine, as a result of its good commercial availability and the high reactivity of its two chlorine atoms.

The substitution reaction of the two halogen atoms of the pyrimidine by the two triazole cycles is very fast due to the very powerful electro-attracting mesomeric effect of the nitro group. Therefore this reaction can be performed at ambient temperature, preferably in the presence of a compound able to trap the hydrochloric acid formed during the reaction. This compound can in particular be a tertiary amine, such as triethyl amine.

In order to carry out the reaction, use is generally made of a solvent of the starting products in which 4,6-di-2-(5-nitro-1,2,4-triazole)-5-nitropyrimidine is insoluble. For example, said solvent can be an alcohol, such as 2-propanol.

The reaction between the 4,6-dihalogeno-5-nitropyrimidine and the 5-nitro-1,2,4-triazole leads to a mixture of the two isomers, which are differentiated by the presence of one or two intramolecular hydrogen bonds between the central nitro group and the two hydrogen atoms of the triazole cycles. These two isomers are in accordance with the following formulas:

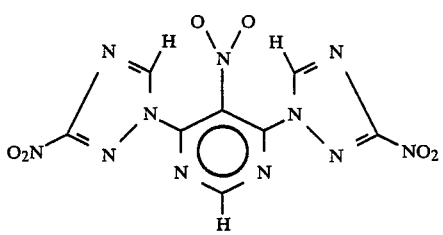

(I$_a$)

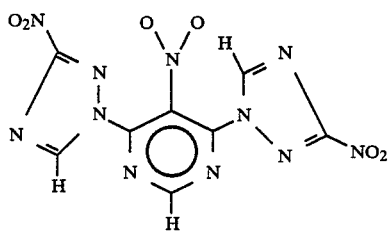

(I$_b$)

The isomer of formula I$_b$, which is thermodynamically less stable, is very much in the minority. Thus, it is sufficient to recrystallize in acetonitrile the product obtained by the reaction between the compounds of formulas II and III in order to make the isomer of formula I$_b$ disappear to the advantage of the isomer of formula I$_a$.

The pyrimidine derivative according to the invention can be used as an explosive material. In this case, said derivative is generally dispersed in a thermoplastic or thermosetting binder optionally containing other conventionally used additives in such compositions, such as plasticizers and the like.

Other features and advantages of the invention can be gathered from the following example given in an illustrative and non-limitative manner.

This example illustrates the preparation of 4,6-di-2-(5-nitro-1,2,4-triazole)-5-nitropyrimidine from 4,6-dichloro-5-nitropyrimidine, which is commercially available, and 5-nitro-1,2,4-triazole, which is prepared from 5-amino-1,2,4-triazole.

I. Preparation of the 5-nitro-1,2,4-triazole.

1.68 g (0.02 mole) of 5-amino-1,2,4-triazole are dissolved in 16 ml of glacial acetic acid and the solution obtained is added to a solution constituted by 7 ml of concentrated H$_2$SO$_4$ and 1.6 g (0.023 mole) of sodium nitrite NaNO$_2$.

The mixture is kept at a temperature between 0° and 5° C. After 5 min, 50 ml of water are added, whilst maintaining the temperature at about 0° C.

The solution obtained is added to 200 ml of 10% sodium nitrite heated to 45° to 50° C. After one hour at 45° C., the solution is acidified with 0.6 ml of H$_2$SO$_4$ and is then treated with 1.2 g of urea.

The 5-nitro-1,2,4-triazole is then extracted with ethyl acetate and is recrystallized in methanol. Its melting point is 210° C. The reaction yield is 57%.

II. Preparation of 4,6-di-2-(5-nitro-1,2,4-triazole)-5-nitropyrimidine.

$5.10^{-3}$ mole of 4,6-dichloro-5-nitropyrimidine are dissolved in 15 ml of 2-propanol and refluxing takes place. $1.1.10^{-3}$ mole of 3-nitro-1,2,4-triazole are dissolved in 25 ml of 2-propanol and 1.6 ml of triethylamine and said mixture is added to the dichloronitropyrimidine solution.

A precipitate very rapidly forms, which is filtered and washed abundantly with 2-propanol and water. This product is then purified by solubilization in acetone followed by reprecipitation with water. The product is filtered and recrystallized in acetonitrile. The yield is 74%.

The elementary analysis of the product obtained is as follows:

|  | C | H | N |
|---|---|---|---|
| Found | 27.66 | 0.91 | 44.15 |
| Calculated | 27.52 | 0.87 | 44.12 |

The product obtained is in the form of a crystalline white solid, whose melting point is 248° C. Its density, measured with the gas pycnometer, is $\rho = 1.74$.

It is soluble in acetone, methylethylketone, ethyl acetate, acetonitrile, dimethyl acetamide, dimethyl formamide (DMF), dimethyl sulphoxide (DMSO) and nitrobenzene. It is insoluble in water, alcohols, chlorinated solvents and benzene. Its specific surface is 2.70 m$^2$/g (measured by the BET method).

It has the following properties:

I. Spectroscopic properties. (1) Nuclear magnetic resonance (NMR)

By adopting the following notations for the different nuclei of the molecule:

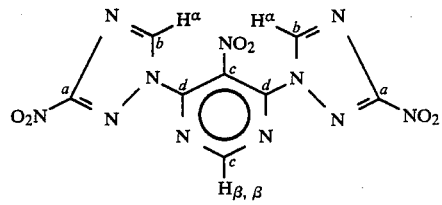

the results obtained in NMR are as follows:
(a) NMR of the proton $^1$H

The $^1H$ proton spectrum at 60 MHz of the sample dissolved in dimethyl sulphoxide (DMSO $d_6$) has two peaks: 1 peak at 10,000 ppm corresponding to the H ($\alpha$) protons of the triazole cycle in a hydrogen bond with the nitro group and 1 peak at 9.46 ppm due to the H ($\beta$) proton at 2 of the pyrimidine cycle.

These peaks are characteristic of the isomer (A) having two intramolecular hydrogen bonds:

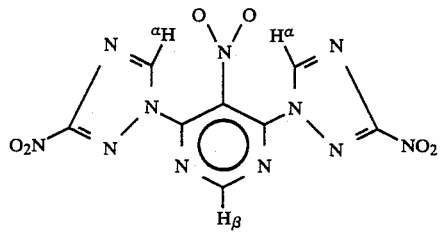

(A)

In the case of a sample not recrystallized in aceto nitrile, the presence of a small percentage of the isomer (B) only having a single intramolecular hydrogen bond leads to the appearance of two small supplementary peaks:

9.54 ppm H ($\beta'$) of the pyrimidine cycle and 8.96 ppm H ($\alpha'$) of the triazole cycle not involved in the hydrogen bond:

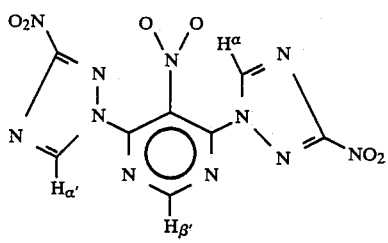

(B)

(b) NMR carbon $^{13}C$

The spectrum at 20.15 MHz of the sample dissolved in acetone $d_6$ in the presence of a relaxing agent constituted by chromium acetylacetonate gives the following chemical displacements:

| δ (ppm) | Attribution | |
|---------|-------------|---|
| 165.20 | $C_{(a)}$ | C—$NO_2$ (triazole) |
| 159.20 | $C_{(c)}$ | C—H (pyrimidine) |
| 148.51 | $C_{(b)}$ | C—H (triazole) |
| 148.33 | $C_{(d)}$ | C—NTr (pyrimidine) |
| 125.31 | $C_{(e)}$ | C—$NO_2$ (pyrimidine) |

The infrared spectrum reveals a group of difficulty attributable bands indicating the presence of nitro aromatic cycles. The C-H band of triazole appears at 3150 $cm^{-1}$.

II. Thermal and explosive properties. (1) Oxygen balance

The oxygen balance with respect to $CO_2$ and $H_2O$ is $-55.78g$ of $O_2$ for 100 g of product. For comparison, the oxygen balance of TATB is $-55.81$ g/100 g, whilst that of octogen is $-21.6$ g/100 g.

(2) Deflagration temperature.

An approximately 20 mg sample in stainless steel container is immersed in a bath, whose temperature is raised at 5° C./min. In the present case, the temperature at which the product deflagrates is 356° C.

(3) Thermal induction time.

Approximately 10 mg of product in a steel container are suddenly introduced into a bath at the measuring temperature and the time at which decomposition occurs is recorded. Taking the kinetics to be approximately zero, it is possible to calculate the activation energy. For 4,6-di-2-(5-nitro-1,2,4-triazole)-5-nitropyrimidine, deflagration occurs after 5s for a temperature of 380° C. The activation energy of the reaction is 39.7 kcal/mole.

(4) Detonation velocity.

The detonation velocity calculated on the basis of the formula according to the empirical method of Rothstein and Petersen described in Propellants and Explosives 4, pp. 56–60, 1979 is 8420 m/s for the crystal density. For comparison and using the same method, the calculated detonation velocity of TATB is 7870 m/s and that of octogen is 9050 m/s.

(5) Shock sensitivity

The shock sensitivity of the product was determined with the aid of a pendulum ram weighing 5 kg, a 30 mg sample being placed on sandpaper. The test was carried out in accordance with the Bruceton method.

Under such test conditions, no pyrotechnic reaction was obtained for the maximum height of the pendulum: H>72 cm.

For comparison purposes, the shock sensitivity of TATB corresponds to $H_{50}$>72 cm and that of octogen to $H_{50}$ 15 cm. Thus, 4,6-di-2-(5-nitro-1,2,4-triazole)-5-nitropyrimidine has a very low shock sensitivity, whilst being able to supply a high energy.

We claim:
1. 4,6-di-2-(5-nitro-1,2,4-triazole)-5-nitropyrimidine of formula:

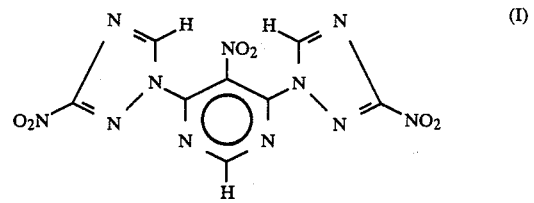

(I)

in the form a pure isomer or mixtures of isomers.

2. Isomer of 4,6-di-2-(5-nitro-1,2,4-triazole)-5-nitropyrimidine of formula:

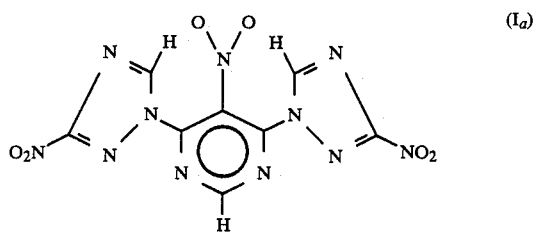

($I_a$)

* * * * *

UNITED STATES PATENT AND TRADEMARK OFFICE
CERTIFICATE OF CORRECTION

PATENT NO. : 4,970,312

DATED : November 13, 1990

INVENTOR(S) : Jean-Paul Freche et al.

It is certified that error appears in the above-identified patent and that said Letters Patent is hereby corrected as shown below:

Column 2, line 3, delete "lll" and insert --III--.

Column 2, line 4, delete "ll" and insert --II--.

At Column 3, Formulas (Ia) and (Ib) should read:

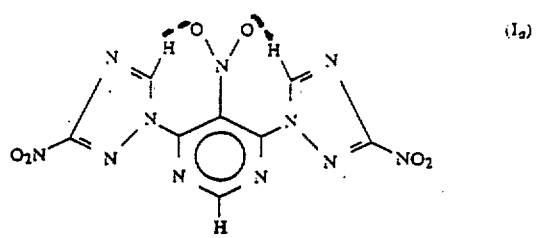

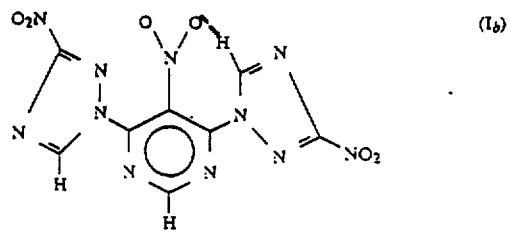

UNITED STATES PATENT AND TRADEMARK OFFICE
CERTIFICATE OF CORRECTION

PATENT NO. : 4,970,312

DATED : November 13, 1990

INVENTOR(S) : Jean-Paul Freche et al.

It is certified that error appears in the above-identified patent and that said Letters Patent is hereby corrected as shown below:

At Column 5, Formulas (A) and (B) should read:

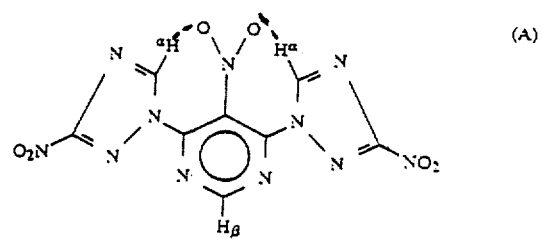

(A)

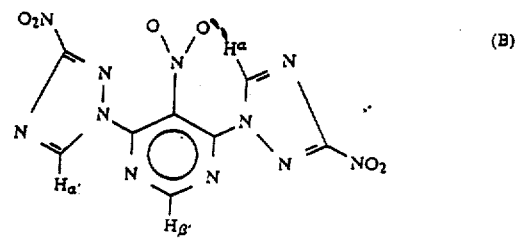

(B)

UNITED STATES PATENT AND TRADEMARK OFFICE
CERTIFICATE OF CORRECTION

PATENT NO. : 4,970,312

DATED : November 13, 1990

INVENTOR(S) : Jean-Paul Freche

It is certified that error appears in the above-identified patent and that said Letters Patent is hereby corrected as shown below:

At Column 6, Claim 2, Formula (Ia) should read:

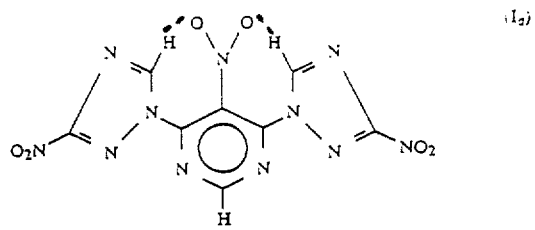

Signed and Sealed this

Twenty-eighth Day of April, 1992

Attest:

HARRY F. MANBECK, JR.

Attesting Officer

Commissioner of Patents and Trademarks